Figure 3:
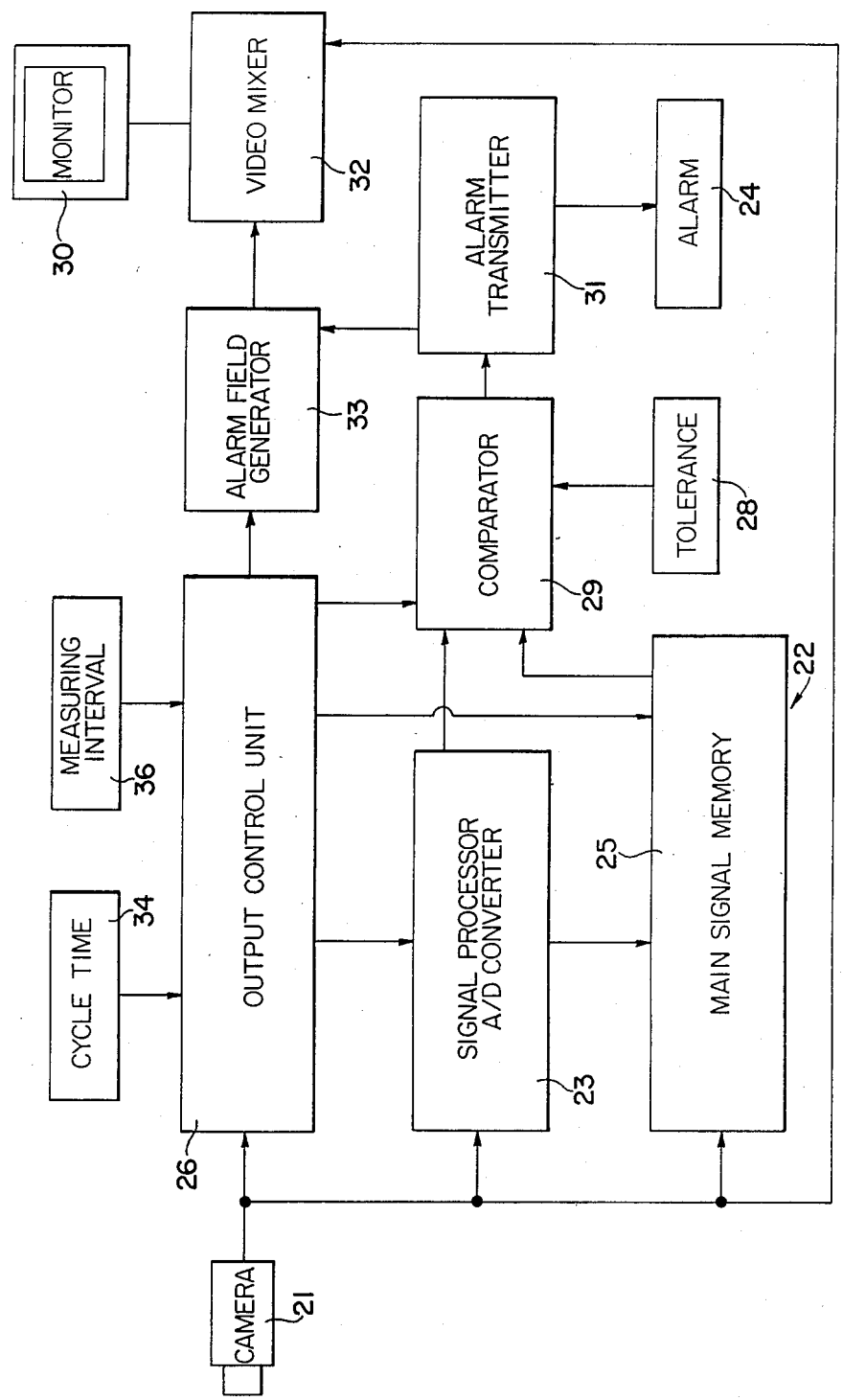

United States Patent [19]

Krieg et al.

[11] Patent Number: 4,902,137
[45] Date of Patent: Feb. 20, 1990

[54] METHOD AND APPARATUS FOR THE DETERMINATION OF FOREIGN BODIES IN FLUIDS

[75] Inventors: Gunther Krieg; Gerhard Barth, both of Karlsruhe; Eberhard Vaas, Pforzheim; Manfred Reiser, Winnenden-Hertmannsweiler, all of Fed. Rep. of Germany

[73] Assignee: Harro Hofliger Verpackungsmasghinen GmbH, Allmersbach im Tal, Fed. Rep. of Germany

[21] Appl. No.: 152,329

[22] Filed: Feb. 4, 1988

[30] Foreign Application Priority Data

Feb. 4, 1987 [DE] Fed. Rep. of Germany ....... 3703306

[51] Int. Cl.$^4$ ...................... G01N 21/89; G01N 21/90
[52] U.S. Cl. ................................. 356/427; 250/223 B; 356/240
[58] Field of Search .............................. 356/240, 427; 250/223 B

[56] References Cited

U.S. PATENT DOCUMENTS

| | | | |
|---|---|---|---|
| 3,963,348 | 6/1976 | Nakatani et al. | 356/240 X |
| 4,050,824 | 9/1977 | Woodrow et al. | 356/427 |
| 4,274,745 | 6/1981 | Takahashi et al. | 356/427 |
| 4,547,067 | 10/1985 | Watanabe | 356/240 X |

FOREIGN PATENT DOCUMENTS

| | | | |
|---|---|---|---|
| 2246458 | 4/1973 | Fed. Rep. of Germany | 356/427 |
| 3043031 | 6/1982 | Fed. Rep. of Germany. | |
| 3145686 | 3/1983 | Fed. Rep. of Germany. | |
| 2036301 | 6/1980 | United Kingdom | 356/240 |

Primary Examiner—Vincent P. McGraw

[57] ABSTRACT

A method is proposed for detecting foreign bodies in fluids to investigate the fluids such as infusion liquids for foreign bodies which can lead to the plugging of infusion needles or other dangers for a patient. In the method light is directed onto the fluid and the light departing from this fluid is detected. The fluid is illuminated evenly with polarized light, and the light penetrating through the fluid is further dimmed by further polarization. The light intensity of individual measuring regions is measured through photo-electric sensing and the measured intensity is compared with an adjustable threshold so that when the threshold is exceeded at any given time during a measuring interval, corresponding signals are produced.

16 Claims, 2 Drawing Sheets

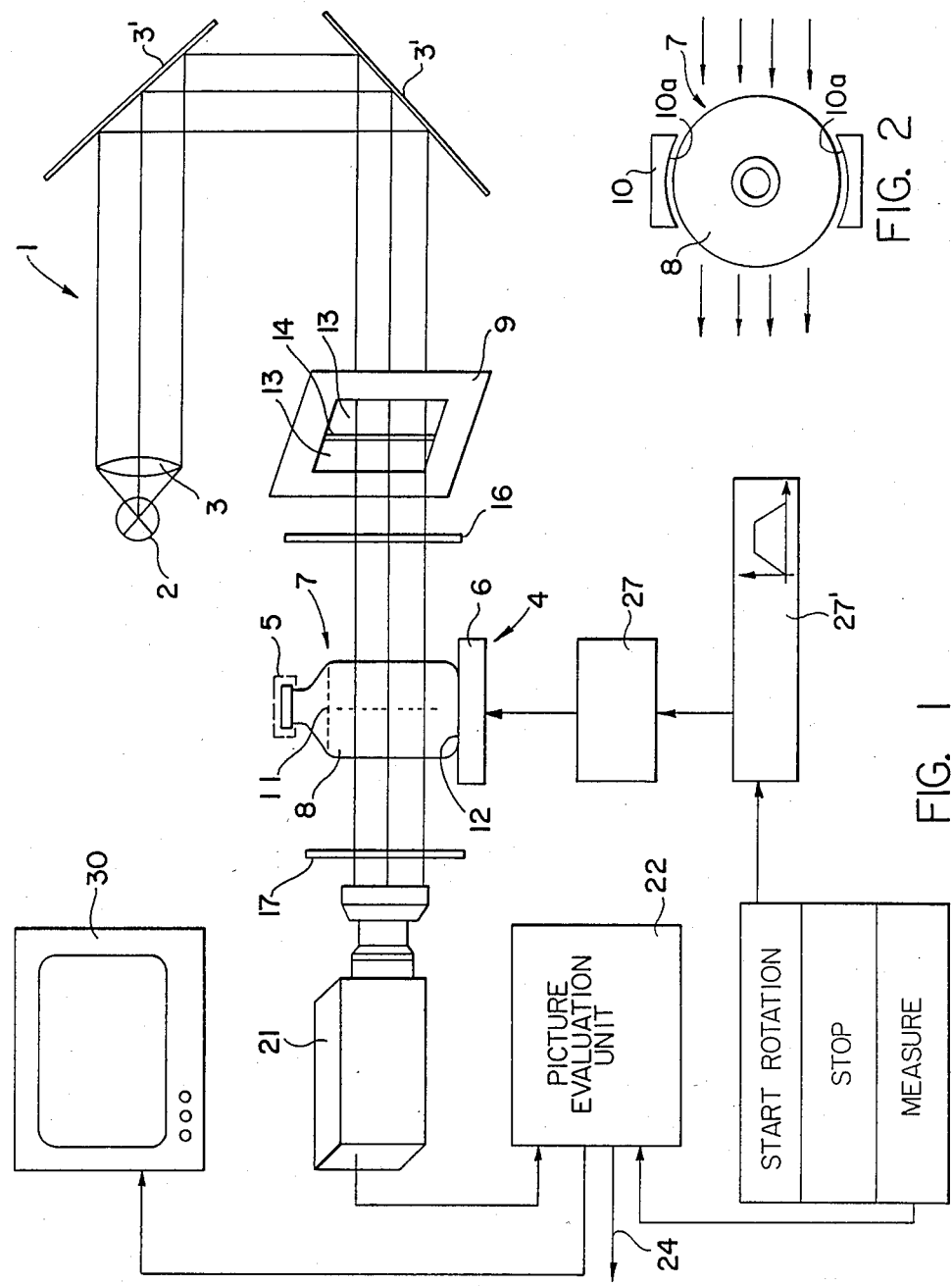

METHOD AND APPARATUS FOR THE DETERMINATION OF FOREIGN BODIES IN FLUIDS

The invention comprises of a method for detecting foreign bodies in fluids, in particular in bottles containing liquids such as infusion solutions or the like, in which the fluid is evenly illuminated with polarized light and the light penetrating the fluid is observed through a crossed analyser by which the light incident upon the fluid is further dimmed.

With infusion liquids, in particular infusion bottles, which hold a quantity of at least 100 milliliters, however as a rule several hundred milliliters and typically 1 liter, a problem arises in that foreign particles can get into the infusion fluid, as for example rubber or cork particles from closures, metal particles, or threads and the like. These types of foreign particles of a certain size, approximately 50 micrometers, create the danger that they will plug up the bore of an infusion needle. Further, a risk can occur to a patient if this type of relatively large particle gets into the bloodstream. It is therefore necessary to examine infusion bottles for foreign particles up to a large size so that the infusion bottles with large foreign particles can be sorted out while the bottles with smaller particles can be retained. Individual or a few foreign particles over a particular size can also be in other fluids, which should be understood here to include liquids and gases, whether these flow in a conduit or are perceived discretely as annoyances in the contents as bottles are packed, so that the separating process should be introduced.

It is known for ampules, which are cut from glass, formed by melting and then are closed and which hold only a small amount of liquid, a maximum of 50 millimeters, to be illuminated through a polarization filter and then to be observed by means of an analyzer at an acute angle to the axis of the light falling upon the ampule in order to separate out defective ampules. The subjective observation is tiresome for the observer and is associated with considerable uncertainty, and it may be that only small vessels such as even ampules will be observed which are manufactured in the manner described hereinafter from glass of good optical quality. With infusion bottles which consist of poured glass and, with this, relatively poor optical quality, this subjective procedure leads to unreliable results since on the one hand the bottle to be observed is too large and with this the relevant particles in the peripheral regions will be overlooked, and on the other hand surprisingly bottles will be unjustifiably separated out because of glass defects.

German Patent DE-OS No. 31 45 668 proposes a device for optical examination of fluid containers for foreign bodies with a laser, whose beam is directed onto a cylindrically shaped reflecting surface, is reflected from this surface and is dispersed in a plane (also a light curtain) which illuminates the liquid in a linear configuration whereby a row of light sensitive detectors is arranged behind the fluid in the plane extending through the light curtain. A particle getting into the dispersed laser beam causes it to be dimmed which should be established through photo elements as a departure from the normal illumination. This known device did not deliver satisfactory results, for example, because the measured results were not particle dependent and the laser intensity falling off at the upper and lower ends corresponding to a Gaussian distribution did not make the necessary detection certainty possible in these regions.

In a similar manner it is known from U.S. Pat. No. 4,274,745 to focus light attenuated through a slit and passing through an ampule on a row of detectors and to detect the intensity. For this it is likewise valid apart from the foregoing that only vessels with small volumes can be examined. It was further tried to spread a laser beam likewise in a plane as a light curtain, to direct the beam onto the infusion bottle and to capture the dispersed light by means of a T.V. camera for evaluation. Here the light source and the camera were not aligned with the bottle of liquid to be examined but were arranged at an angle. This dispersed light process did not yield any particle-size-dependent measurements.

The invention has as an object a method and an apparatus for objectively detecting foreign bodies in fluids, in particular to cause a reliable discrimination of particles according to their size over larger observation surfaces of more than 20 square centimeters, preferably more than 50 square centimeters.

According to the invention the above-mentioned problem is solved by means of a process which is characterized in that the fluid is observed close to the optical axis of the light falling upon the fluid and the light intensity of individual measuring zones is detected by means of electro-optical conversion, the measured intensity at a given time is compared with an adjustable value and when the value is exceeded during a measuring interval, corresponding signals are produced at the same time. A device according to the invention provides a solution to the problem in that the light source, and if necessary supplemental optical elements, illuminates the fluid evenly since a polarizer is arranged in front of the fluid, an analyzer behind the fluid, and a television camera as the detection device is arranged at the side of the fluid diametrically opposite from the light source.

In contrast to the known objective processes, the invention causes the observation to take place in the dark field of the old subjective process. Since the particles in the liquid are not self-illuminating and they are also not phosphorescent, it is possible to make the background as viewed from the camera as dark as possible and yet however achieve a point-like brightness with the presence of particles. This is achieved through two crossed polarizers, and if necessary with due consideration being given to the optical activity of the fluid itself, the polarizers are adjustable such that their polarization directions (with non-optical liquids) run perpendicular to one another. With this the background is considerably dimmed. Foreign particles in the liquid disperse not only the light but also surprisingly raise the mentioned polarization of light through the first polarizer by a considerable amount and bring about therefore a de-polarization so that the television camera can establish an intensive light spot through the light dispersed by the particles. The largest distributed brightness and the best monotone response to the distributed light intensity for the particle size is produced in the forward dispersion direction for the particles (large) of interest here. So for that reason the optical positioning of the light source, the distribution cell and the camera should preferably be in direct alignment. The dispersion cell, that is a bottle to be examined, should therefore be observed on the optical axis of the incident light in the direction opposite to the light. Also, in order to be able to work with cylindrical bottles, which produce a brightness on the optical axis, at high amplification, preferably with the largest opening at which the camera can work, a preferred embodiment provides that the region of the optical axis of the light beam is dimmed or correspondingly, with a convex enveloping surface surrounding the fluid, an attenuator or aperture extending parallel to the axis of the enveloping surface is provided centrally in front of this surface between the surface and the light source or the camera.

Very small angular departures are, of course, not damaging. These can range up to a maximum of 10° with ordinary liquids; however, they should not lie above this level, since on the one hand the intensity of the light dispersed from the interested particles diminishes, and on the other hand dispersed light from bubbles, glass defects and so on increases. If the camera is arranged with the above-mentioned cylindrical surfaces outside of the central region and the brilliant regions caused by the bottle, the intermediate attenuator can be omitted.

Satisfactory signals are produced with incoherent light. This can be white or colored light, if necessary by means of colored filters. In the latter case the influence on detection caused by foreign light, such as day light, is considerably suppressed. Light impenetrable encapsulation of the system can then arise—in contrast to the use of white light from an incandescent lamp. A color filter can be placed, for example, in front of the objective lense of the camera.

On account of the polarization of a laser beam, it is not necessary to place a polarizer in front of the measuring zone with the insertion of a laser as the light source. An interference filter in front of the objective lense of the camera can sharply reduce the sensitivity to scattered light.

The high intensity of the laser beam produces a good signal-to-noise ratio. Besides a He/Ne-laser, consideration can also be given to an Argon-Ion laser or a YAG-laser.

Until now it was thought that for detection of the annoying particles, the resolution of the camera must lie in the range of the size of the particles of interest (see typically DE-OS No. 30 43 031). This leads to the fact that on the one hand only a small cross-sectional surface can be examined—and with this only ampules—not however larger bottles. While on the other hand the evaluation area was considerable and many calculations as well as a long time were needed. In contrast a further highly preferred embodiment provides that the intensities of several sensing pixels are combined for formation of a measuring zone, that is averaging by addition. A measuring zone consists therefore of individual sensing points in an ordinary television camera, preferably in the order of magnitude of 30×30. This means a simplification of the further processing of the measured intensities is achieved without fear of an information deficiency.

The camera sees namely the scattered light not only at a sensing point (pixel), but on the basis of the scattering effect, lack of sharpness and preferably exceptional maximum resolution of the camera, wherever an increased light intensity is also established over several sensing points of the television camera by small particles. This preferred embodiment makes possible real-time processing with a quality calculator such as in particular a standard table calculator like a personal computer.

Since at the free upper surfaces of fluids, in particular liquids, or more generally at the boundary surface or interface between two fluids (be they liquids or gases), the upper or boundary surfaces can move and cause reflections and measuring errors, it is provided in a further embodiment that the free upper surface of the fluid is screened from the light beam or correspondingly an attenuator is provided in front of the upper surface of the fluids. Also in order to avoid disturbances from the remaining peripheral regions, in particular boundary surfaces with the surrounding bottle or glass envelope, pipe or the like, which generally are less critical, further embodiments provide that the peripheral regions of the fluids will be screened or correspondingly that a mask covering the peripheral regions of the fluid is arranged in front of the illuminated surface of the fluid. The screening of certain peripheral regions by means of masks or screens is not critical, as long as they are actually relatively small and away from these surfaces, since the foreign particles move in the fluid and the measurement time on any given occasion can be so selected that a moving foreign particle to be detected can be established in each case. A measuring time of 1 second is clearly sufficient. This is true in particular again if the fluid is set in motion, preferably rotation, in which case it can particularly happen that a rotating plate is provided in order to set the liquid in motion. A further configuration provides that the fluid is set in motion with a controlled increasing speed or correspondingly that the rotatable plate is set into a motion of this type such that its speed varies continuously and steadily. By means of these embodiments those foreign particles which have settled to the bottom of the vessel are stirred up and by their movement can also be detected. In contrast to ampules however, a considerable splashing occurs with larger containers, such as with infusion bottles, with the ordinary horizontal guidance of the bottles to the measuring cell. So if the dispersed light reflections, which are almost certain here, are to be avoided, the screening of the observed region is necessary and thus again the danger is increased that relevant foreign particles will remain behind the screen and will not be detected. As a solution to this problem it is provided in accordance with a further important aspect of the invention that the container of the measuring cell is guided vertically. In order to keep the measurement free of vibrations of other devices such as conveyors, it is provided that the measuring device is separated and decoupled from the other apparatus such as even the conveyors which in particular do not consist of common frames, supports and the like but are connected only to the common foundation. The bottles to be examined are transferred for measurement by means of a conveyor holding element of the measuring device and then are released from the conveyor so that they likewise are no longer in communication with the structure. The conveyor can therefore be a paternoster or elevator which preferably grips the bottles around the neck below the closure by means of a fork. In the measuring cell the bottles can be placed at a discharge point, however, are preferably engaged by two cups which simultaneously form vertical edge blinds. In each case the elevator fork is released from the bottle top and then sets the bottle free in the measuring cell so that the measurement can be accomplished.

In a preferred embodiment it is provided that at least two detections at a time are undertaken in each zone, the intensity for each zone is stored, the intensity of a later detection is compared with the stored intensity and a signal is produced by the deviation of the intensity difference above a threshold value. A method of this type is well known in which however non-polarized light is directed from below against the bottom of an ampule and is observed at a right angle to the optical axis of the light falling upon the ampule. A satisfactory discrimination of the foreign particles of interest with the previous invention is not possible with this state of the art. Also here the intensity values of the individual measuring pixels were processed which required a considerable time and equipment expense, and likewise made the examination of small ampules possible only in the best of circumstances.

Further advantages and features of the invention are revealed by the claims and the following specification in which an exemplary embodiment of the invention is described with reference in particular to the drawings. These are:

FIG. 1 - a schematic illustration of the construction of the device in accordance with the invention.

FIG. 2 - a plan view of another holder of a bottle to be inspected in the measuring cell, and FIG. 3 - a block diagram for outputting the evaluation from the picture-evaluation unit.

A device according to the present invention comprises a light source 2 in the form of an incandescent lamp. This can be arranged behind a lens system 3 for projecting parallel light. A reversing mirror 3' guarantees a compact configuration of the device. A fluid, in particular a liquid, is guided through a measurement cell 4 or is brought into the cell. In the illustrated embodiment the measuring cell consists of a rotating plate 6, an infusion bottle 7 set up with an infusion solution 8, the bottle being placed in rotation and finally halted again, whereby the measurement is accomplished with the liquid rotating. Instead of this the bottles can also be rotated on the aforementioned rotation device when the device is remote from the measuring cell in order that the liquid in the bottle is set into rotation and finally the bottle is brought into the measuring cell 4. In both cases the bottles 7 can be held by the neck by means of an interchangeable adaptor 5 or by a clamping cup 10 on the main body (FIG. 2) whereby the clamping cup 10 forms lateral blinds 10a. As described in greater detail below, together with similar interchangeable masks 9, different bottles can be suitably accommodated. Further, a liquid stream can be guided through the measuring cell, for example in a pipe or a channel which consists of transparent windows on the sides facing toward the light source and facing away from the source.

In the illustrated exemplary embodiment a mask 9 is arranged in front of the measuring cell 4—the mask being drawn in perspective solely for illustration, actually however being situated perpendicular to the beam or to the line connecting the light source and camera. The mask screens a part of the light beam or correspondingly covers a part of the bottle 7. This is true in particular for the region of the upper surface of the liquid 8 in the bottle 7 since, due to movements of the upper surface, reflections would be produced back into the liquid which, due to further reflections, could lead to a disturbance of the measurement. If necessary the floor or bottom region of the bottle can also be covered. With cylindrical bottles such as illustrated in FIG. 1, it turns out that with otherwise symmetrical illumination of the bottle a bright overexposed stripe occurs parallel to the axis of the bottle when an observation is made on the optical axis of the incident light along the connecting line between the light source and the axis of the bottle. For this reason the mask 9 is divided into two windows 13 which are separated from one another by means of a intermediate attenuating strip 14. A first polarizer 16 is arranged perpendicular to the direction of the light beam in front of the cell—toward which the mask 9 can be brought—and a further polarizer or analyzer 17 is arranged behind the measuring cell. Behind the analyzer 17 in the direction of the light beam relative to the measuring cell a television camera 21 is arranged diagonally opposite the light source 2. The television camera is connected with a picture evaluation unit 22. This evaluation unit is connected to a monitor 30. The evaluation unit comprises an output 24 over which the unit produces a signal, in particular a control signal for an ejection chute for culling out bad bottles. With the illustrated embodiment having a rotatable plate 16 arranged under the measuring cell on which a bottle 7 is placed, an output control 26 is provided which on the one hand controls a motor 27 of the rotatable plate 6 by means of a drive control 27' and on the other hand controls the picture evaluation unit 22.

The picture evaluation unit 22 consists of a signal processor 23 with an analog-to-digital convertor. The signals received from the individual measuring cells in the camera are added up or averaged over a larger measuring zone of, for example $30 \times 30$ measuring pixels, and are further processed as such a summed signal. A main signal memory 25 is connected to the signal conditioning circuit 22 on the one hand and on the other hand a comparator 29 is connected with the output. The comparator 29 likewise has an input for an output signal from the main signal memory 25. Further, a tolerance indicator or threshold setting circuit 28 is connected to the comparator. An alarm transmitter 31 follows the comparator, and to this on the one hand an alarm signaling unit 24, which controls for example the ejection chute in the conveyor for the bottles by means of a control signal. The signal from the camera 21 is further connected to the video mixer 32 which on the other hand also receives a signal from the alarm transmitter 31 by way of an alarm field generator 33. The cycle time can be sent to the discharge unit 26 by means of the input 34, and the desired measuring signal can be sent by means of the input 36 (FIG. 3).

The measuring cell 4 is illuminated with light from the light source 2. The polarizers 16, 17 are so adjusted relative to one another that if necessary during consideration of an optically active fluid in the bottle 7, the intensity of the light passing through the analyzer 17 and falling on the camera 21 is minimal.

The bottle 7 is put into rotation by a motor for a predetermined time by means of the discharge control in which the rotation is preferably produced with a controlled increasing and subsequently a continually decreasing speed so that abrupt motions and vibrations are avoided. By this means small particles which have settled to the bottom of the bottle are stirred up and swirled through the liquid so that they will be detected in their movement. At the conclusion of the rotation and if necessary after a certain waiting time for the liquid motion to come to rest, since the fluid continues to turn in the bottle after the rotating plate 6 and the bottle 8 have come to a rest, measurements are taken during a predetermined measuring interval, that is, the picture evaluation unit 22 is activated.

The signal from the camera 21 is first sent to the monitor 30 by means of the video mixer 32 so that from time to time the picture of the examined bottle 7 can be permanently observed there.

During a measuring interval the picture captured by the camera is sent to the signal conditioning circuit 23 and is there digitized. The digitized signal is sent to the main signal memory and is stored there. The digital signal is further sent periodically, for example every 50 ms., to the comparator 29 to which the picture stored in the main signal memory 25 is likewise sent by means of the output control unit 26. In the comparator 29 the difference at various times is detected, the corresponding picture sections (measuring zones) are compared with one another and it is determined if the difference lies above or below an externally supplied tolerance or threshold value. This threshold value corresponds to a particular brightness difference and therefor is a gauge for the particle sizes (at least hypothetically for the same types of particles).

If the signal difference exceeds the tolerance value then on the one hand an alarm signal is given, if necessary in the form of a control signal for a particular ejection chute in further conveying of the bottles, so that the bottle which has caused the signal can be ejected. On the other hand in the preferred and illustrated embodiment the signal is sent to an alarm field generator 33 which produces a mark on the monitor 30 in the measuring zone or correspondingly the picture section in question by means of the video mixer 32. In this manner, the location where a foreign particle was detected is indicated.

The picture evaluation unit therefore compares in the comparator 29 the brightness of the individual zones of the picture received by the camera 21 or correspondingly those deviations, which are established by means of a difference amplifier, with a pre-established threshold, corresponding to a desired tolerance, from the threshold sender 28. If the threshold is exceeded the picture evaluation unit 22 produces a signal by means of the alarm conductor 24. In this manner there can be an acoustical or optical signal that indicates that the bottle just examined is not in order and therefore is to be ejected. For automatic passing or ejecting bottles there can be a control signal which operates an ejection chute by which the defective, just-examined bottles are diverted from the conveyor path for the bottles found to be in order.

It is proposed that with the occurrence of larger foreign particles in liquids, in particular with large aperture openings, these point-like particles cause a considerable brightness in the camera picture which can be detected through the picture evaluation unit and can be processed in the described manner. This brightness can be clearly established on the monitor 30. It is further proposed that the brightness with substantially larger particles is greater than with smaller particles, so that by this means a selection of the bottles can be undertaken according to size of the foreign bodies detected in them. In particular it is proposed that a threshold value of this type be set so that the particles which for example are larger than 50 micrometers (taking into consideration the tolerances) produce a control signal over the control conductor 24, the smaller particles, however do not. With this for example the limit is set so low for infusion solutions that infusion bottles found to be good contain no particles which would lead to clogging of the infusion needle or endangerment of the patient due to thrombosis, which should be avoided. On the other hand, the size also must not be set so low that the number of bottles rejected would be too large, although these bottles in the best of circumstances will contain particles which are not critical. It has been shown that a device according to the present invention makes possible the selection with satisfactory preciseness.

With abrupt increases in intensity due to a foreign particle in the liquid during the practice of the process according to the present invention, the increased intensity is essentially increased not only in one raster point or in an area of the receiving tube corresponding to the size of a particle and making contact with the electron beam, but in a larger region of a plurality of raster points in an ordinary T.V. camera. Correspondingly the same is true with the camera having CCD's wherein however a Vidicon, in particular a Z-Vidicon or Novicon is preferred above all with larger bottles since it makes possible a sensitivity many times higher than with a CCD-camera.

As stated therefore, in a preferred embodiment of the picture evaluation system the individual raster points of the television camera are combined in larger evaluation regions which, for example, consists of 30×30 raster points. Within the regions the intensities of the individual raster points can be averaged and an average total intensity is detected and further processed. This contributes to a simplification of the further processing and to a reduction of the processing expense.

What is claimed is:

1. The method for detecting particles in a moving fluid provided in a stationary containment vessel and comprising the following steps:
    providing light transparent windows in the fluid containment vessel one of which windows is an entry window and has a generally convex external surface and the other window being an exit window and oriented on an optical axis through said windows,
    directing a polarized beam along the optical inspection axis and through the entry and exit windows provided on this axis,
    masking the window in an area where the light beam is generally perpendicular said convex window surface so that all of the polarized light entering the moving fluid is refracted at least slightly by the stationary convex entry window,
    cross polarizing the light exiting the exit window so that the light beam consists only in that part of the polarized light beam that has been unpolarized by particles in the fluid or by defects in or on the transparent windows,
    providing a video camera for the cross polarized light beam,
    comparing the video output from successive video frames to provide an indication of the particles in the moving fluid.

2. The method according to claim 1 wherein said masking step comprises placing an opaque screen between the vessel and the incoming polarized light beam, the screen defining two openings with a portion of the screen blocking the polarized light beam in an area oriented parallel to the convex window surface area that is oriented perpendicular to the light beam optical axis.

3. The method according to claim 2 wherein the stationary vessel is a cylindrical container, spinning the container to cause the fluid contents to swirl, and holding the container stationary at an inspection station with its axis oriented perpendicular to the polarized light beams optical axis and with the area parallel the window defining a line parallel the axis of the cylindrical vessel.

4. The method according to claim 1 further characterized by digitizing the video outputs from the video camera and storing these digitized video outputs in a computer's memory.

5. The method according to claim 4 further characterized by the step of programming the computer to include a threshold defining parameter for the comparison step so that only moving particles above a predetermined size will be detected.

6. The method according to claim 1 further characterized by the step of adjusting the intensity of the polarized light beam so as to minimize the intensity of the light sensed by the video camera thereby increasing the contrast between the illuminated particles and the surrounding fluid in said successive video output frames.

7. The method according to claim 5 further characterized by adjusting the intensity of the polarized light beam to minimize the intensity of the light sensed by the video camera and to heighten the contrast between the surrounding fluid and the illuminated articles as represented by said digitized video output signals.

8. The method according to claim 7 further characterized by generating a reject signal when a moving particle above said predetermined size is detected.

9. The method according to claim 8 wherein said predetermined size is larger than 50 micrometers.

10. The method according to claim 3 further characterized by incrementally moving the cylindrical container parallel to its axis in order to inspect axially spaced zones corresponding to the window openings referred to above.

11. Apparatus for detecting articles in a moving fluid, said apparatus comprising, means for directing a light beam along an optical axis oriented generally perpendicular to inspection station axis, polarizing means for said light beam, means defining an inspection station and defining entry and exit windows in a fluid containment vessel one of which windows has a generally convex external shape and the other window being oriented in spaced relationship relative to the entry window on said optical inspection axis, means for blocking the polarized light beam along a line oriented generally perpendicular to said optical inspection axis so that the polarized light beam entering the moving fluid is refracted slightly by the convex stationary entry window, means for moving the fluid while holding the containment vessel in a stationary condition during an inspection sequence, a cross polarizing device on said optical inspection axis outside the exit window for cross polarizing the light exiting the window to pass only that part of the polarized light that has been "unpolarized" by particles in the fluid or by defects in the windows, video camera means for detecting cross polarized light and means for comparing the video output from successive video frames from said camera to provide indication of the particles in the moving fluid.

12. The apparatus according to claim 11 wherein said means for blocking polarized light comprises and opaque screen defining two side-by-side laterally spaced openings, said containment vessel comprising a generally cylindrically shaped transparent container having a central axis oriented perpendicular said optical axis, said side-by-side windows being defined in part by an elongated masking line oriented parallel to the container axis.

13. The apparatus according to claim 12 further characterized by means for digitizing the video output signals from the video camera and for storing at least one such video output signal.

14. The apparatus according to claim 13 further characterized by a computer programmed to include a threshold defining parameter for comparing successive video signals so that only moving particles above a predetermined size will be detected, and means for generating a reject or alarm signal when said predetermined particle size is exceeded.

15. The apparatus according to claim 14 further characterized by means for varying the intensity of the light beam to adjust the intensity of the light sensed by the video camera in a particular inspection procedure.

16. The apparatus according to claim 15 further characterized by means for incrementally moving the cylinder container between successive video comparison procedures to achieve an inspection of discrete regions within said cylindrical container.

* * * * *